United States Patent

Kiguchi et al.

[11] 4,228,183
[45] Oct. 14, 1980

[54] NOVEL PHENETHYLAMINE DERIVATIVES AND PROCESSES FOR PREPARING SAME

[75] Inventors: Tasaburo Kiguchi, Osaka; Kimiaki Hayashi, Nara; Isao Yamaguchi, Tokyo, all of Japan

[73] Assignee: Tanabe Seiyaku Co., Ltd., Osaka, Japan

[21] Appl. No.: 45,955

[22] Filed: Jun. 6, 1979

[30] Foreign Application Priority Data

Jun. 30, 1978 [JP] Japan .................................. 53/79938

[51] Int. Cl.³ ..................... A61K 31/265; C07C 69/96
[52] U.S. Cl. ..................................... 424/301; 260/463
[58] Field of Search .......................... 260/463; 424/301

[56] References Cited

U.S. PATENT DOCUMENTS

| | | | |
|---|---|---|---|
| 2,400,038 | 5/1946 | Buck et al. | 260/463 |
| 3,801,624 | 4/1974 | Biel et al. | 260/463 |
| 3,869,492 | 3/1975 | Biel et al. | 424/301 |
| 4,033,997 | 7/1977 | Roteman | 260/463 |
| 4,051,169 | 9/1977 | Saari | 424/301 |

OTHER PUBLICATIONS

R. Morrison et al., Organic Chemistry, Allyn & Bacon, Inc. Boston (1967), pp. 954–956.
Abstract of Amer. Chem. Soc. (Div. of Med. Chem.) 165 Nat'l. Meeting No. 11 (1973).
Pharmacologist 16, 268 (1974).

Primary Examiner—Donald G. Daus
Assistant Examiner—M. C. Eakin
Attorney, Agent, or Firm—Bierman & Bierman

[57] ABSTRACT

A compound of the formula:

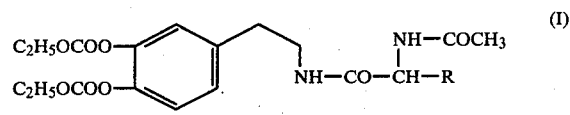

wherein R is methyl or 2-methylthioethyl, is prepared by either (A) condensing a compound of the formula:

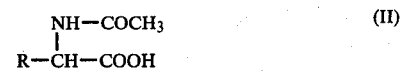

wherein R is the same as above, or a reactive derivative thereof with 3,4-diethoxycarboxyphenethylamine, or (B) condensing the compound (II) or a reactive derivative thereof with dopamine, followed by reacting the resultant product with an ethoxycarbonyl halide. The compound (I) shows potent renal blood flow-increasing activity and is useful for the treatment of renal hypertension, congestive heart failure and other diseases due to renal blood flow disturbances.

5 Claims, No Drawings

NOVEL PHENETHYLAMINE DERIVATIVES AND PROCESSES FOR PREPARING SAME

This invention relates to a novel phenethylamine derivative and processes for preparing same. More particularly, it relates to the phenethylamine derivative of the formula:

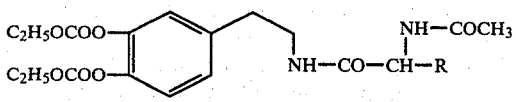

wherein R is methyl or 2-methylthioethyl.

It is known that 3,4-dihydroxyphenethylamine (hereinafter referred to as "dopamine") is useful for the treatment of shock or oliguria evoked by a variety of causes such as surgical operation or myocardial infarction because, unlike other catecholamines (e.g., isoproterenol, adrenaline, noradrenaline), dopamine shows potent renal vasodilating activity and is effective in increasing the renal blood flow. It is also known that dopamine may be used for the treatment of renal failure, hypertension, chronic congestive heart failure and other diseases. However, for these medicinal uses dopamine is still unsatisfactory in that it is slightly absorbed from digestive organs and can be used only in the form of an injection. Moreover, when administered intravenously to a living body, dopamine is rapidly inactivated with monoamine oxidase or other enzymes in the liver and shows only a short duration of action. In view of these drawbacks of dopamine itself, therefore, dopamine derivatives which can be used by oral administration have been reported up to now. For example, N-L-alanyldopamine [i.e., N-(L-alanyl)-3,4-dihydroxyphenethylamine], N-DL-methionyldopamine [i.e., N-(DL-methionyl)-3,4-dihydroxyphenethylamine] and N-L-isoleucyl-dopamine [i.e., N-(L-isoleucyl)-3,4-dihydroxyphenethylamine] are disclosed in Pharmacologist 16, 268(1974), Japanese Patent Publication (unexamined) No. 11922/1972 and American Chemical Society (Division of Medicinal Chemistry) 165 National Meeting No. 11 (1973).

As a result of various investigations, we have now found that the compound (I) of the present invention shows potent renal blood flow-increasing activity for a long period of time and is useful for the treatment of renal hypertension, congestive heart failure and other diseases due to renal blood flow disturbances. For example, when the effect of each test compounds on the renal blood flow are estimated by administering them duodenally to dogs at a dose of 23.73 $\mu$mols/kg, the renal blood flow-increasing activity of N-(N-acetyl-L-methionyl)-3,4-diethoxycarboxyphenethylamine of the invention is about 2 times stronger than that of N-L-alanyldopamine disclosed in Japanese Patent Publication (unexamined) No. 11922/1972 and lasts for a period about 2.5 times as long as that of the latter compound. The compound (I) of the invention when administered orally is well absorbed from digestive organs and shows the long-lasting therapeutic effects without substantially affecting the blood pressure and heart rate. In addition, since the compound (I) is chemically stable, said compound is gradually converted to free dopamine in the tissues without being rapidly metabolized in the digestive organs and/or liver. Apparently, these favorable properties of the compound (I) of the invention are quite surprising findings because no significant blood flow-increasing activity can be observed in such analogous compounds as N-(N-acetyl-L-glycyl)-3,4-diethoxycarboxyphenethylamine, N-(N-acetyl-L-valyl)-3,4-diethoxycarboxyphenethylamine, N-(N-acetyl-L-isoleucyl)-3,4-diethoxycarboxyphenethylamine and N-($\alpha$-formyl-L-isoleucyl)-3,4-diethoxycarboxyphenethylamine which differ from that of the present invention only in the amino acid moieties thereof. Further, the toxicity of the compound (I) of the present invention is considerably low. For example, when N-(N-acetyl-L-methionyl)-3,4-diethoxycarboxyphenethylamine of the invention is administered intravenously to mice at a dose of 2800 mg/kg (i.e., 5.95 mmols/kg), no mouse dies during the period of 7 days after the administration.

According to the present invention, the compound (I) can be prepared by:

(A) condensing an N-acetylamino acid of the formula:

wherein R is the same as defined above, or a reactive derivative thereof with 3,4-diethoxycarboxyphenethylamine, or (B) condensing the N-acetylamino acid (II) or a reactive derivative thereof with dopamine to give a phenethylamine derivative of the formula:

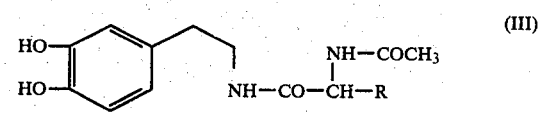

wherein R is the same as defined above, followed by reacting the phenethylamine derivative (III) with an ethoxycarbonyl halide.

For the purpose of the present invention, 3,4-diethoxycarboxyphenethylamine and dopamine may be employed in the form of either a free base or an acid addition salt thereof. Suitable examples of said acid addition salt include hydrochloride, hydrobromide and p-tosylate. Ethoxycarbonyl chloride and ethoxycarbonyl bromide are suitable as the ethoxycarbonyl halide of the invention. Further, the reactive derivative of the above-mentioned acid (II) includes, for example, the corresponding mixed anhydride (e.g., lower alkoxycarbonyl esters such as ethoxycarbonyl, isobutoxycarbonyl, tert.-butoxycarbonyl and tert.-amyloxycarbonyl esters) and active ester (e.g., esters with N-hydroxysuccinimide, N-hydroxyphthalimide, 1-hydroxybenzotriazole and p-nitrophenol). The mixed anhydride of the acid (II) may be prepared in conventional manners, for example, by reacting the acid (II) with a lower alkoxycarbonyl halide (e.g., ethoxycarbonyl chloride, isobutoxycarbonyl chloride, sec.-butoxycarbonyl chloride, ethoxycarbonyl bromide) at 20° to −20° C., preferably at about 5° C., in the presence of an acid acceptor (e.g., triethylamine, tributylamine, pyridine) in a solvent. Chloroform, tetrahydrofuran, toluene, methylenechloride and dioxane are suitably employed as the solvent. On the other hand, the active ester of the acid (II) may be prepared by reacting said acid with N-hydroxysuccinimide, N-hydroxyphthalimide, p-nitrophenol or the like at 20° to −10° C., preferably at about 0° C., in the presence of a dehydrating agent (e.g., dicyclohexylcarbodiimide) in a solvent (e.g., tetrahydrofuran, dioxane, dimethoxyethane, methylenechloride).

The condensation reaction of the acid (II) with 3,4-diethoxycaboxyphenethylamine, dopamine or their acid addition salt can be readily accomplished. For example, said condensation reaction is preferably carried out in the presence of a dehydrating agent in a solvent. Suitable examples of said dehydrating agent include dicyclohexylcarbodiimide, 1-ethyl-3-(3-dimethylaminopropyl)-carbodiimide and so forth. Dioxane, tetrahydrofuran and methylenechloride are suitable as the reaction solvent. Said condensation reaction may be especially preferably carried out in the presence of an acid acceptor such as triethylamine, tributylamine or pyridine. It is preferred to carry out the reaction at 20° to −10° C., especially at 0° to −5° C.

On the other hand, the condensation reaction of the reactive derivative of the acid (II) with 3,4-diethoxycarboxyphenethylamine, dopamine or their acid addition salt can be carried out at a temperature of 20° to −10° C., especially at 5° to −5° C., in a solvent. Tetrahydrofuran, dioxane, dimethylformamide, chloroform and acetonitrile are suitable as the reaction solvent.

When dopamine or an acid addition salt thereof is employed as one of the starting materials of the invention, the phenethylamine derivative (III) obtained may be isolated and purified in conventional manners or may be used in the form of a crude product for the subsequent step.

The reaction of the phenethylamine derivative (III) with the ethoxycarbonyl halide can be carried out in the presence of an acid acceptor in a solvent. Suitable examples of the acid acceptor include triethylamine, tributylamine and pyridine. Chloroform, tetrahydrofuran, pyridine and dimethylformamide are suitable as the solvent. It is preferred to carry out the reaction at −10° to 30° C., especially at 0° to 10° C.

The compound (I) of the present invention thus obtained shows potent renal blood flow-increasing activity and is useful to improve renal functions. Moreover, because the compound (I) of the invention when administered orally shows excellent chemical stability, long-lasting therapeutic effects and low side effects, said compound is especially suitable for use by oral administration. The dose of the compound (I) to be administered may vary depending on the kinds and degree of diseases to be treated, but the preferred daily dose of said compound may be about 0.5 to 50 mg/kg/body. The compound (I) may be administered either orally or parenterally. For oral administration, it can be used in the form of tablets, powders, capsules, liquids, syrups, emulsions, suspensions or the like. For parenteral administration, said compound can be used in the form of injections, suppositories or the like. The pharmaceutical preparations may be made by using conventional pharmaceutical carriers such as, for example, excipients (e.g., crystalline cellulose, calcium citrate, lactose), disintegrators (e.g., cellulose calcium glycolate, corn starch), binding agents (e.g., hydroxypropyl-cellulose, polyvinylpyrrolidone, white dextrin), lubricants (e.g., talc, magnesium stearate), emulsifiers (e.g., sorbitan fatty acid esters, sodium alkylsulfate, polyoxyethylene sorbitan fatty acid esters, lecithin), solvents (e.g., water, ethanol) and the like.

EXPERIMENTS

Male dogs weighing about 15 kg were anesthetized with pentobarbital sodium (i.v.). Under artificial respiration thereof the left renal artery was exposed through a frank incision, and a flow probe was placed on the artery. The renal blood flow was measured with a short wave-magnetic flow meter. Besides, the blood pressure was measured with a pressure transducer through a catheter inserted into the femoral artery, and the heart rate was measured simultaneously with a tachograph.

Each test compounds were dissolved or suspended in pure water and administered into the duodenum as a model of oral administration. (During the experiments, pentobarbital sodium was infused intravenously at a rate of 4 mg/kg/hour to keep the dogs in deep anesthesia).

The experimental results are shown in the following Table.

TABLE

| Test compounds* | Number of dogs used | Dose (μmols/kg) | Increase (%) in renal blood flow | Duration of action (minutes) |
|---|---|---|---|---|
|   | 5 | 2.64 | 13 ± 2.9 | 68 ± 4.9 |
| 1 | 5 | 7.91 | 19 ± 4.6 | 110 ± 19.0 |
|   | 5 | 23.73 | 26 ± 7.4 | 127 ± 15.6 |
|   | 4 | 2.64 | 13 ± 3.4 | 87 ± 18.9 |
| 2 | 5 | 7.91 | 21 ± 2.1 | 147 ± 25.0 |
|   | 5 | 23.73 | 39 ± 5.5 | 194 ± 30.0 |
|   | 4 | 2.64 | 6.1 ± 1.3 | 28 ± 7.7 |
| 3 | 5 | 7.91 | 14.7 ± 2.7 | 66 ± 9.3 |
|   | 5 | 23.73 | 19.8 ± 2.6 | 72 ± 6.6 |

Note:
Test compounds* :
The compounds of the present invention
No. 1 : N-(N-acetyl-L-alanyl)-3,4-diethoxycarboxyphenethylamine
No. 2 : N-(N-acetyl-L-methionyl)-3,4-diethoxycarboxyphenethylamine
Known compound:
No. 3 : N-L-alanyldopamine As seen in the Table, Compound Nos. 1 and 2 of the present invention showed remarkable increase in the renal blood flow, and said renal blood flow-increasing activity of Compound Nos. 1 and 2 were apparently stronger than that of Compound No. 3. Particularly, the renal blood flow-increasing activity of Compound No. 2 of the invention lasted for a period about 2 to 3 times as long as that of Compound No. 3. Additionally, at every dose of the experiments Compound Nos. 1 and 2 showed no significant change in the blood pressure and heart rate.

Practical and presently-preferred embodiments of the present invention are shown in following Examples. Throughout the specification and claims, the term "lower alkoxy" should be interpreted as referring to alkoxy having one to five carbon atoms.

EXAMPLE 1

2.62 g of N-acetyl-L-alanine are suspended in 26 ml of anhydrous chloroform, and 2.02 g of triethylamine are added thereto under ice-cooling. The mixture is stirred. 9.39 g of 3,4-diethoxycarboxyphenethylamine p-tosylate are added to the mixture, and a solution of 4.13 g of dicyclohexylcarbodiimide (hereinafter referred to as "DCCD") in 20 ml of anhydrous chloroform is added dropwise thereto. The mixture is stirred at room temperature for 4 hours. After the reaction is completed, said mixture is filtered. The filtrate is washed with water, diluted hydrochloric acid and water, successively. Then, the filtrate is dried and condensed to remove solvent. The oily residue thus obtained is purified by silica gel column chromatography (solvent: chloroform-acetone(7:3)), crystallized with n-hexane and then collected by filtration. The crude crystals thus obtained are recrystallized from a mixture of ethyl acetate and n-hexane. 4.43 g of N-(N-acetyl-L-alanyl)-3,4-diethoxycarboxyphenethylamine are obtained as colorless needles. M.p. 84°–86° C. Yield: 54%.

IR$\nu_{max.}^{KBr}$ (cm$^{-1}$): 3300, 1780, 1675, 1650.

$[\alpha]_D^{20}$ −25.5° (C=2, methanol).

EXAMPLE 2

3.82 g of N-acetyl-L-methionine are suspended in 38 ml of anhydrous chloroform, and 2.02 g of triethylamine are added thereto. The mixture is stirred. After the mixture is cooled to −5° C., 2.88 g of ethoxycarbonyl chloride are added dropwise thereto, and the mixture is further stirred at the same temperature for 30 minutes. Then, the mixture is cooled to −5° to 0° C., and a solution of 9.39 g of 3,4-diethoxycarboxyphenethylamine p-tosylate in 40 ml of anhydrous chloroform and a solution of 2.02 g of triethylamine in 1.5 ml of anhydrous chloroform are added dropwise thereto. The resultant mixture is stirred at the same temperature for 1.5 hours and allowed to stand at 0° C. overnight. After the reaction is completed, the mixture is washed with water, diluted hydrochloric acid and water, successively. The reaction mixture is dried and condensed to remove solvent. The oily residue thus obtained is treated in the same manner as described in Example 1. 4.63 g of N-(N-acetyl-L-methionyl)-3,4-diethoxycarboxyphenethylamine are obtained as colorless crystals. M.p. 85°–90° C. Yield: 49%.

IR $\nu_{max.}^{KBr}$ (cm$^{-1}$): 3300, 1780, 1670–1640.

$[\alpha]_D^{20}$ −15.6° (C=2, methanol).

EXAMPLE 3

N-(N-acetyl-L-alanyl)-3,4-diethoxycarboxyphenethylamine is obtained from N-acetyl-L-alanine in the same manner as described in Example 2. Yield: 68% The physico-chemical properties of this product are identical with those of the sample obtained in Example 1.

EXAMPLE 4

2.87 g of N-acetyl-L-methionine and 1.73 g of N-hydroxy-succinimide are dissolved in 29 ml of dioxane, and a solution of 3.1 g of DCCD in 10 ml of dioxane is added thereto under ice-cooling. The mixture is stirred at room temperature for one hour and allowed to stand overnight. After the reaction, the mixture is filtered. The filtrate is condensed under reduced pressure. The residue thus obtained is crystallized with ether and recrystallized from isopropanol. 2.64 g of N-hydroxysuccinimide ester of N-acetyl-L-methionine are obtained. M.p. 109°–111° C.

2.16 g of the above-mentioned succinimide ester and 3.52 g of 3,4-diethoxycarboxyphenethylamine p-tosylate are dissolved in 22 ml of anhydrous chloroform, and 0.76 g of triethylamine is added thereto under ice-cooling. The mixture is stirred for 4 hours. The reaction mixture is washed with water, diluted hydrochloric acid and water, successively. Then, the mixture is dried and condensed to remove solvent. The oily residue thus obtained is treated in the same manner as described in Example 2. 2.54 g of N-(N-acetyl-L-methionyl)-3,4-diethoxycarboxyphenethylamine are obtained. Yield: 72% The physico-chemical properties of this product are identical with those of the sample obtained in Example 2.

EXAMPLE 5

4.19 g of N-acetyl-L-alanine, 3.68 g of N-hydroxysuccinimide, 6.7 g of DCCD and 42 ml of dioxane are treated in the same manner as described in Example 4, whereby 5.9 g of N-hydroxysuccinimide ester of N-acetyl-L-alanine are obtained. M.p. 125°–127° C.

3.8 g of dopamine hydrochloride are dissolved in 20 ml of dimethylformamide, and 4.56 g of the above-mentioned succinimide ester and 4 g of triethylamine are added thereto under ice-cooling and under nitrogen gas atmosphere. The mixture is stirred for 15 hours. Then, the mixture is filtered, and the filtrate is condensed under reduced pressure. The oily residue thus obtained is washed with ether and dissolved in a small amount of water. The aqueous solution is allowed to stand at room temperature overnight. Crystalline precipitates are collected by filtration and recrystallized from ethanol. 4.8 g of N-(N-acetyl-L-alanyl)-dopamine are obtained as colorless needles. M.p. 200°–202° C. Yield: 90% 2.64 g of said N-acetylalanyldopamine are dissolved in 26 ml of pyridine, and 2.51 g of ethoxycarbonyl chloride are added dropwise thereto under stirring and ice-cooling. The mixture is allowed to stand at room temperature overnight, and then condensed under reduced pressure to remove pyridine. Ethyl acetate is added to the residue, and the mixture is washed with water, diluted hydrochloric acid and water, successively. Then, the mixture is dried and condensed to remove solvent. The oily residue thus obtained is crystallized with ethyl acetate. Crystalline precipitates are collected by filtration and recrystallized from a mixture of ethyl acetate and n-hexane. 3.4 g of N-(N-acetyl-L-alanyl)-3,4-diethoxycarboxy-phenethylamine are obtained. Yield: 83% The physico-chemical properties of this product are identical with those of the sample obtained in Example 1.

EXAMPLE 6

2.85 g of dopamine hydrochloride, 4.32 g of N-hydroxysuccinimide ester of N-acetyl-L-methionine, 3.04 g of triethylamine and 15 ml of dimethylformamide are treated in the same manner as described in Example 5. After the reaction, the mixture is condensed under reduced pressure to remove solvent. The residue is dissolve in ethyl acetate, washed with water and dried. The solution is condensed to remove solvent. 3.1 g of N-(N-acetyl-L-methionyl)-dopamine are obtained as caramel.

2.2 g of said N-acetyl-methionyldopamine, 1.61 g of ethoxycarbonyl chloride and 22 ml of pyridine are treated in the same manner as described in Example 5. The crude product thus obtained is purified by silica gel column chromatography (solvent: chloroform-acetone(7:3)) and crystallized with n-hexane. The crystals thus obtained are collected by filtration and recrystallized from a mixture of ethyl acetate and n-hexane. 2.1 g of N-(N-acetyl-L-methionyl)-3,4-diethoxycarboxyphenethylamine are obtained. Yield: 66% The physico-chemical properties of this product are identical with those of the sample obtained in Example 2.

What we claim is:

1. A compound of the formula:

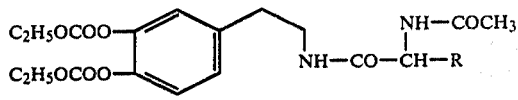

wherein R is methyl or 2-methylthioethyl.

2. The compound of claim 1, in which R is 2-methylthioethyl.

3. The compound of claim 1, in which R is methyl.

4. A laevorotary isomer of the compound claimed in any one of claims 1, 2 or 3.

5. A pharmaceutical composition for increasing renal blood flow activity which comprises a compound of the formula:

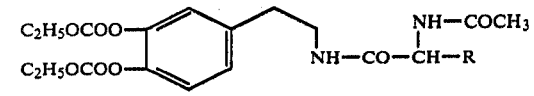

wherein R is methyl or 2-methylthioethyl, in an amount sufficient to provide a therapeutic effect when administered, and a pharmaceutically acceptable carrier therefor.

* * * * *